United States Patent [19]

Porter

[11] Patent Number: 5,374,425
[45] Date of Patent: Dec. 20, 1994

[54] ANIMAL FEED ADDITIVES

[76] Inventor: William L. Porter, Animax Ltd., Gilray Road, Vinces Road Industrial Estate, Diss, Norfolk, England

[21] Appl. No.: 54,470

[22] Filed: Apr. 27, 1993

Related U.S. Application Data

[63] Continuation of Ser. No. 613,272, Nov. 13, 1990, abandoned, which is a continuation-in-part of Ser. No. 358,555, May 26, 1989, abandoned, which is a continuation-in-part of Ser. No. 152,018, Feb. 3, 1988, abandoned.

[30] Foreign Application Priority Data

Feb. 20, 1987 [GB] United Kingdom ............... 8704058

[51] Int. Cl.$^5$ .............................................. C12N 1/20
[52] U.S. Cl. .............................. 424/93.45; 424/195.1; 424/93.462; 426/2
[58] Field of Search .............. 424/93 C, 93 G, 93 H, 424/93 J, 93 K, 93 M, 195.1; 426/2; 435/252.4, 252.9, 253.4, 804

[56] References Cited

U.S. PATENT DOCUMENTS

| 4,299,858 | 11/1981 | Aubert et al. | 435/804 |
| 4,710,379 | 12/1987 | Kawai et al. | 424/93 H |

FOREIGN PATENT DOCUMENTS

| 0107415 | 9/1978 | Japan | 424/93 D |
| 0131917 | 8/1983 | Japan | 424/93 H |
| 0020220 | 2/1984 | Japan | 424/93 J |
| 0084825 | 5/1984 | Japan | 424/93 H |
| 800104 | 8/1980 | Netherlands | 424/93 J |

OTHER PUBLICATIONS

Wolter et al., Recueil de Medecine Veterinaire 163(12):1131–1138 (1987).

Primary Examiner—Douglas W. Robinson
Assistant Examiner—Jean C. Witz
Attorney, Agent, or Firm—Edwin D. Schindler

[57] ABSTRACT

A method of manufacture of an animal feed additive for promoting weight gain wherein selected non-pathogenic bacteria are grown in a liquid culture, the bacterial cells are isolated from the bulk of the fluid substrate and are killed by application of heat, and the isolated killed cells are combined with a carrier to provide a solid or liquid feed additive.

17 Claims, No Drawings

ANIMAL FEED ADDITIVES

RELATED APPLICATIONS

This is a continuation of application Ser. No. 07/613,272filed Nov. 13, 1990, now abandoned, which is a continuation-in-part of application Ser. No. 07/358,555, filed May 26, 1989, now abandoned, which, in turn, is a continuation-in-part of application Ser. No. 07/152,018 filed Feb. 3, 1988, now abandoned.

FIELD TO THE INVENTION

This invention relates to the manufacture of an animal feed additive which improves the capacity of a foodstuff to produce weight gain in animals, including humans.

BACKGROUND OF THE INVENTION

Known animal feed additives include probiotic products for oral administration, either specifically or by inclusion in feed, and consist of fermented cultures of non-pathogenic bacteria, typically lactobacilli and/or streptococci.

Probiotics are used to improve rate of growth and feed conversion efficiency in young animals and to reduce incidence of enteritis and diarrhoea. However, the effects of such products are highly variable.

The essential mode of action of probiotics is not, in fact, understood. It is commonly thought that they enhance the numbers of non-pathogenic bacteria in the gut, which may assist digestion, possibly through enzyme production, and also increase competition with populations of potentially harmful bacteria such as *Escherichia coli*. However, this is not proved. In fact, the normal dosage of a probiotic is usually insufficient to add appreciably to the intestinal population and this casts doubt on the commonly believed mode of action referred to.

Most importantly, since the mode of action is not in fact sufficiently understood, meaningful quality control of probiotic products is virtually impossible.

A principal object of this invention is to provide an animal feed additive and economical method of manufacture thereof based on improved knowledge of the source of the beneficial effects of cultures of non-pathogenic bacteria. This permits meaningful assay and hence meaningful quality control.

Prior art

U.S. Pat. No. 4,021,303 discloses a method of treatment of microorganisms to extract the useful protein content thereof for the purpose of providing a food supplement. As with previous proposals with this aim, an essential feature is the rupturing of the cell membranes of the microorganisms, more especially by grinding or other mechanical means. The patent proposes chemical treatment of the microorganisms with an alkali prior to mechanical rupturing of the cells, thereby to minimise degradation of the protein during the subsequent cell rupturing step and also to improve the efficiency of the rupturing process.

BRIEF SUMMARY OF THE INVENTION

According to one aspect of the invention, there is provided a method of producing a feed additive which improves the capacity of a foodstuff to produce weight gain in animals, including humans, comprising the steps of:

1) preparing a base culture;
2) sterilizing the base culture;
3) innoculating the base culture with an active starter culture in the form of non-pathogenic bacterial cells;
4) allowing the culture to ferment at least until the rate of bacterial cell growth starts to decline;
5) isolating the cells from the bulk of the fluid substrate; and
6) heating the residue of cells to not less than 100 degrees C. for a period between 5 and 45 minutes, thereby to kill the cells.

The invention also relates to an animal feed additive for promoting weight gain, when produced by the afore-described method.

Application of heat may be, more particularly, by boiling or autoclaving. At normal atmospheric pressure, heat up to a minimum of 100 degrees C. for a period of at least 5 minutes is necessary for beneficial results, and heating to an even higher temperature such as at least 110 degrees C. by autoclaving is most advantageous. In a preferred heating step, the residue of cells is heated in an autoclave to a temperature of at least about 120 degrees C., at a pressure of at least 5 p.s.i., for about 20 minutes.

The invention differs from U.S. Pat. No. 4,021,303 in that the heat treatment, although effective to kill the cells, is specifically not intended to produce rupturing of the cell membranes. The Applicant has found that killing the cells by a combination of sonication and mechanical shearing, instead of heat treatment, does not produce the beneficial results in accordance with the invention.

It will be understood that, conventionally, probiotic products are products containing live bacteria. The product in accordance with the present invention contains only killed bacteria, but nevertheless is a product intended for use as an animal feed additive in analogous manner to certain known probiotics, but specifically for the purpose of improving the capacity of a foodstuff to promote weight gain in animals.

The animal feed additive produced by the method of the present invention can take several forms. Thus, for example, the heat killed cells, in the form of a wet slurry, can have a bacteriostat added thereto for storage and administration in the wet state. Alternatively, the heat killed cells can be dried ready for use, or additionally mixed with wheat bran or finely ground cereal to form an animal feed additive. Yet again, the heat killed cells can be absorbed in a drying agent, such as expanded mica, to produce a concentrated animal feed additive.

Non-pathogenic bacterial cells which may be included in the liquid culture employed in this invention include lactobacilli, bacillus subtills, non-pathogenic streptococcus, bifidobacterium, micrococci and pediococci. In the case of bacillus subtills, or any other sporulating bacteria, the fermentation step is stopped prior to consumption of all the nutrients and the onset of sporulation.

The fermentation step is preferably carried out with the culture at about 35 to 45 degrees C. for a duration of between 24 and 72 hours. The pH value of the culture is preferably maintained at a value between 5 and 7.

A preferred cell separation step comprises adding a flocculating agent, to the fermented culture, allowing the cells to settle, and decanting the bulk of the fluid substrate.

The animal feed additive in accordance with the invention has been tested on chicks in trials lasting 14 days or more. Different groups of chicks were fed a basic diet as a control diet and other diets having allegedly beneficial additives, the additive for one group being the animal feed additive in accordance with the invention. Trials were initially carried out using a commercial broiler feed as a control diet, to assess the effects of differing allegedly beneficial additives. Additives used were live bacterial probiotics known by the Trade Marks Pronifer and Maxipro. The growth and feed conversion efficiency of groups of chicks receiving these products were compared with similar groups of chicks receiving the same originally live bacterial products, but where the products had been subject to autoclaving so as to kill the bacterial cells present in the products. It was found that substantially improved results were obtained when the live bacterial probiotics were autoclaved, thus killing all bacteria present. Further trials were then carried out in which bacterial cultures were used as additives, both as whole cultures and after centrifugal separation into the bulk liquid substrate and the cellular concentrate or residue of killed bacteria. The results were compared against the same control diet as before and also the control diet with added killed yeast cells.

The statistical results of these trials have shown that, especially after a full trial of at least 14 days, the best liveweight gain and best feed conversion ratio is to be expected from the cellular concentrate or residue containing bacteria killed by application of heat. When the live bacterial probiotics were subjected to sonication, thus not only killing the cells but rupturing the cell membranes, a full trial exceeding 14 days showed no benefit in respect of liveweight gain or feed conversion ratio. It thus appears possible that the benefits of the invention are obtained due to a chemical change in one or more cell components which takes place dug to killing the cells by application of heat.

The animal feed additive in accordance with the invention thus has, to an unexpected extent and for an unexpected reason, nutritive benefit to the growth of the animals.

Quality control is enabled firstly because the cellular content of the bacterial culture may be determined in conventional manner before autoclaving, for example colony counting techniques using plate cultures, and secondly because an index of the content is readily obtained either by dry matter estimation of the culture or the concentrated slurry or by using acid or gas production as parameters of bacterial growth.

More generally, various advantages arising from use of the animal feed additive in accordance with the invention are as follows: a) the total cell mass can be estimated and related to the effectiveness of the product; b) stability is improved over conventional probiotics as no live bacteria are present; c) the low volume of the cellular concentrate enables production of a solid, powdered or granular material, when this is required for addition to dry animal feeds; d) liquid products can be manufactured using the heat killed bacterial cells, since the matter is inert (it is difficult to keep cells alive for long periods in a liquid); e) the liquid substrate is a by-product of the method of manufacture which, when used as a bulk liquid feed, is also found to possess useful nutritional properties.

DESCRIPTION OF EMBODIMENT

A practical animal feed additive and method of production thereof in accordance with the invention will now be described by way of example.

First, one exemplary formulation of a base culture will be given:

| | |
|---|---|
| Milk powder | 60 g/l |
| Yeast extract | 4 g/l |
| Sucrose | 10 g/l |
| Beef and vegetable extracts | 1 g/l |
| Vitamin $B_{12}$ | 5 mg/l |
| Magnesium sulphate | 0.2 g/l |
| Manganous sulphate | 0.05 g/l |
| 'Tween 80' (Trade Mark) | 1 m/l |

To the above formulation may be added:

| | |
|---|---|
| D. Potassium H. phosphate | 2.0 g/l |
| Sodium acetate | 5.0 g/l |
| Tri-ammonium citrate | 2.0 g/l, | more especially to act as buffers if pH is not otherwise controlled during the subsequent fermentation process.

The medium is made up to one litre with de-ionised water.

Production of the animal feed additive is then carried out generally in accordance with the following steps:

1. The base culture is mixed using a shearing-type mixer.

2. The culture is sterilized by autoclaving at a pressure not less than 5 p.s.i., conveniently for 15 minutes at 121 degrees C. The culture could be sterilized in other known ways, if desired, which will ensure that any contaminants are killed.

3. The culture is cooled or allowed to cool to about 41 degrees C.

4. The base culture is innoculated with a small volume of an active starter culture, more especially but not exclusively a commercially available strain of a lactobacillus culture (such as *Lactobacillus fermentum* or *Lactobacillus acidophilus* or *Lactobacillus platarum*) or a non-pathogenic streptococcus culture or bacillus subtills culture or a bifidobacterium culture.

5. The culture is allowed to ferment, at a temperature of about 41 degrees C., for a period between 24 and 72 hours, preferably about 48 hours, whilst being subjected to gentle agitation. It will thus be appreciated that fermentation is continued at least until the rate of bacterial growth starts to decline. However, in the case of a sporulating bacteria such as bacillus subtills, fermentation is stopped before all the nutrients are consumed, i.e. before the onset of sporulation.

6. During the fermentation step, a pH value of between 5 and 7, conveniently about 5.5 to 6, is maintained by means of NaOH and/or by means of the buffers previously referred to. If, as is preferred, pH is controlled by use of sodium hydroxide, this may be added initially, and then automatically, responsively to the output of a pH sensor.

7. During the fermentation process, gas production is monitored with a gas flowmeter, acid production is monitored by titration, and optionally cell production may be monitored by cell counting.

8. At the end of the fermentation period, the fermented culture is cooled or allowed to cool to ambient temperature. Settling occurs during this period of cooling.

9. The supernatent liquid is then syphoned off. This leaves a residue in the form of a slurry containing the cells produced by fermentation.

10. The slurry residue is mixed by a shearing-type mixer.

11. The slurry is autoclaved at a pressure of at least 5 p.s.i., typically about 121 degrees C. for between 5 and 45 minutes, preferably 15 to 30 minutes, conveniently say 20 minutes. Autoclaving can be carried out at a higher pressure (and temperature) if desired. The result is a slurry with a high content of killed bacterial cells.

12. The killed cell slurry is again mixed by a shearing type mixer.

13. The killed cell slurry is then dried, as by freeze drying or addition of a bacteriostat and mixing with a drying agent. Again, spray drying, centrifugation, vacuum evaporation or other drying by use of heat may be employed instead, in all cases to produce an animal feed additive ready for use.

14. If desired, the resulting killed cell residue in dried condition may then be combined with an inert carrier to produce a more dilute animal feed additive ready for use. Alternatively, a predetermined quantity of the killed cell concentrate may be mixed whilst simultaneously drying into a given amount of wheat bran, crushed barley or other cereal which is then ground to produce an animal feed additive.

It is alternatively possible to produce a liquid product, again suitable for use as an animal feed supplement, by mixing the wet residue of step 12 or the dried residue of step 13 with a liquid carrier together with a bacteriostat, although a solid product is preferred for inclusion in dry feed.

Alternatively to step 9, a flocculating agent may be employed to effect separation of the cells, reducing the original volume by at least 80 percent.

A cellular concentrate containing only autoclaved cells of Lactobacillus fermentum and added to a basic control diet has been tested on broiler chicks over a period of 0 to 21 days of age with the following results. In the table, the column headings designate the number of parts by weight of cellular concentrate added to one million parts by weight of control feed, and the successive rows in the table indicate weight gain (WG) in grams, weight gain as a percentage of control (WG %), the feed conversion ratio (FCR) and the feed conversion ratio as a percentage (FCR %), taking the FCR for control as 100.

TABLE

|  | 0 | 50 | 100 | 200 | 400 |
| --- | --- | --- | --- | --- | --- |
| WG | 335.25 | 381.08 | 401.81 | 390.52 | 371.36 |
| WG % | 100 | 113.67 | 119.85 | 116.49 | 110.77 |
| FCR | 2.963 | 2.216 | 2.096 | 2.139 | 2.541 |
| FCR % | 100 | 74.79 | 70.74 | 72.19 | 85.75 |

A prototype commercial food additive produced substantially by the method hitherto described has been tested on broiler chicks over a period of 0 to 18 days. The control diet used for this test was a commercially available mix containing wheat (63.4), soya extract (25.0), full fat soya (3.6), dicalcium sulphate (2.0), DL-Methionine (0.22), salt (0.2), Minvite 204 (0.5) and soya bean oil (4.8), with added cholinechloride (0.5), the figures being percentages.

In the following table, the column headings indicate grams/ton of additive employed, first when the fermented slurry residue was autoclaved and second when this residue was boiled.

TABLE

|  | Control | Autoclaved Approx. 30 g/tonne | Boiled Approx. 30 g/tonne |
| --- | --- | --- | --- |
| WG | 360.17 | 381.75 | 376 |
| WG % | 100 | 105.99 | 104.04 |

This result indicates that boiling is nearly as effective as autoclaving as a means of processing the bacterial cells.

A cellular concentrate of autoclaved bacillus subtills cells and added to a basic control diet has also been tested. The addition rate was from 25 milligrams to 800 milligrams per kilogram of feed and maximum weight gain was found to be at an addition rate of between 25 and 200 milligrams per kilogram of feed, with maximum weight gain at about 50 milligrams per kilogram of feed.

A corresponding test, carried out with non-autoclaved bacillus subtills cells, i.e. live cells, obtained by the same fermentation process, resulted in no noticeable weight gain as compared to the basic control diet.

Another corresponding test, using bacillus subtills cells heated to only 80 degrees C. for 15 minutes, resulted in only minimal weight gain.

Further corresponding tests, employing bacillus subtills cells autoclaved for differing periods of 15 minutes, 30 minutes, 45 minutes and 60 minutes, showed that maximum weight gas was achieved with cells autoclaved for a period in the range 15 to 45 minutes, with maximum weight gain when autoclaving had been continued for about 30 minutes. These tests also showed that, with autoclaving for a period of 60 minutes or longer, all beneficial results were lost.

It is also important to note that trials with broiler chicks have been conducted in which WG and FCR were compared when a) the killed cell cellular concentrate was used as a food additive, b) the bulk liquid substrate emerging as a by-product of the process was used as an additive, c) the bulk fermented fluid autoclaved but without separation of the bulk fluid substrate was used as an additive, d) the bulk dried culture without separation and autoclaving was used as an additive, and e) a concentrate of cells killed and ruptured by a combination of mechanical shearing and sonication, but without boiling or autoclaving, was used as an additive. These trials have shown that substantially improved WG and FCR are obtained with the cellular concentrate of cells killed by application of heat, heating being effected up to at least 100 degrees C. for at least 5 minutes. It is therefore to be understood that process step 9) of the above-described method of production, in which the bulk liquid substrate is syphoned off or otherwise removed, is an essential step in production of the animal feed additive in accordance with the invention. Clearly, step 11) of the process, which involves killing the cells by application of heat to the specified extent, is also essential.

The identity of the substance obtained from bacterial cells killed by application of heat and having considerable beneficial effect on animal growth and feed conversion efficiency is not yet known. However, tests for antibiotic activity have proved negative.

It will be understood that various modifications of the above-described method of production are possible within the scope of this invention.

It should also be made clear that the feed additive produced by the method of the invention is useful for administration to animals other than chicks, such as pigs and other monogastrics, as well as ruminants, and also including humans.

I claim:

1. A method of promoting weight gain in animals comprising the steps of:
   preparing a feed additive composition by a method which includes the steps of:
   1) preparing a base medium;
   2) sterilizing the base medium;
   3) inoculating the base medium with an active starter culture in the form of non-pathogenic bacterial cells, said non-pathogenic bacterial cells being selected from the group consisting of *Lactobacillus fermentum*, *Bacillus subtilis* and a combination thereof;
   4) fermenting the culture, at least, until the rate of bacterial cell growth starts to decline;
   5) isolating the cells from the bulk of the fluid substrate; and,
   6) heating the isolated cells from about 100° C. to about 121° C. for a period between 15–30 minutes; and,
   supplementing an animal's diet by including an amount of 50 to 400 ppm by weight of said feed additive composition as a part of said diet.

2. The method according to claim 1, in which step 6) comprises heating the isolated cells in an autoclave to a temperature of at least 110° C.

3. The method according to claim 2, in which step 6) comprises heating the isolated cells in an autoclave to a temperature of at least about 120° C., at a pressure of at least 5 p.s.i., for about 20 minutes.

4. The method according to claim 1, in which step 5) comprises adding a flocculating agent to the fermented culture, allowing the cells to settle, and decanting the bulk of the fluid substrate.

5. The method according to claim 1, in which the non-pathogenic bacterial cells comprise *Bacillus subtilis*, and the fermentation step is stopped prior to the onset of sporulation.

6. The method according to claim 1, in which the fermentation step is carried out with the culture at about 35° to 45° C., for a duration of between 24 and 72 hours.

7. A method according to claim 6, further comprising the step of maintaining the pH value of the culture between a value of 5–7 while carrying out the fermenting step.

8. The method according to claim 1, in which the isolated cells combined with an inert carrier.

9. A method of promoting weight gain in animals comprising the steps of:
   preparing a feed additive composition by a method which includes the steps of:
   1) preparing a base medium;
   2) sterilizing the base medium;
   3) inoculating the base medium with an active starter culture in the form of non-pathogenic bacterial cells, said non-pathogenic bacterial cells include *Bacillus subtilis* in combination with non-pathogenic bacterial cells of the genus *Lactobacilli*;
   4) fermenting the culture, at least, until the rate of bacterial cell growth starts to decline;
   5) isolating the cells from the bulk of the fluid substrate; and,
   6) heating the isolated cells from about 100 ° C. to about 121° C. for a period between 15–30 minutes; and,
   supplementing an animal's diet by including an amount of 50 to 400 ppm by weight of said feed additive composition as a part of said diet.

10. The method according to claim 9, in which step 6) comprises heating the isolated cells in an autoclave to a temperature of at least 110° C.

11. The method according to claim 10, in which step 6) comprises heating the isolated cells in an autoclave to a temperature of at least about 120° C., at a pressure of at least 5 p.s.i., for about 20 minutes.

12. The method according to claim 9, in which step 5) comprises adding a flocculating agent to the fermented culture, allowing the cells to settle, and decanting the bulk of the fluid substrate.

13. The method according to claim 9, in which the non-pathogenic bacterial cells comprises *Bacillus subtilis*, and the fermentation step is stopped prior to the onset of sporulation.

14. The method according to claim 9, in which the fermentation step is carried out with the culture at about 35° to 45° C., for a duration of between 24 to 72 hours.

15. A method according to claim 14, further comprising the step of maintaining the pH value of the culture between a value of 5–7 while carrying out the fermenting step.

16. The method according to claim 9, in which the isolated cells combined with an inert carrier.

17. A method of promoting weight gain in animals comprising the steps of:
   preparing a feed additive composition by a method which includes the steps of:
   1) preparing a base medium;
   2) sterilizing the base medium;
   3) inoculating the base medium with an active starter culture in the form of non-pathogenic bacterial cells, said non-pathogenic bacterial cells are *Bacillus subtilis*;
   4) fermenting the culture, at least, until the rate of bacterial cell growth starts to decline;
   5) isolating the cells from the bulk of the fluid substrate; and,
   6) heating the isolated cells from about 100° C. to about 121° C. for a period between 15–30 minutes; and,
   supplementing an animal's diet by including an amount of 50 to 400 ppm by weight of said feed additive composition as a part of said diet.

* * * * *